United States Patent
Perkó et al.

(10) Patent No.: US 11,504,547 B2
(45) Date of Patent: Nov. 22, 2022

(54) FRACTIONATION SELECTION TOOL IN RADIOTHERAPY PLANNING

(71) Applicants: KONINKLIJKE PHILIPS N.V., Eindhoven (NL); THE GENERAL HOSPITAL CORPORATION, Boston, MA (US)

(72) Inventors: Zoltán Perkó, Cambridge, MA (US); Jan Unkelbach, Cambridge, MA (US); Matthieu Frédéric Bal, Geldrop (NL)

(73) Assignees: KONINKLIJKE PHILIPS N.V., Eindhoven (NL); THE GENERAL HOSPITAL CORPORATION, Boston, MA (US)

(*) Notice: Subject to any disclaimer, the term of this patent is extended or adjusted under 35 U.S.C. 154(b) by 1071 days.

(21) Appl. No.: 16/086,030

(22) PCT Filed: Apr. 10, 2017

(86) PCT No.: PCT/EP2017/058477
§ 371 (c)(1),
(2) Date: Sep. 18, 2018

(87) PCT Pub. No.: WO2017/182300
PCT Pub. Date: Oct. 26, 2017

(65) Prior Publication Data
US 2020/0289848 A1    Sep. 17, 2020

Related U.S. Application Data

(60) Provisional application No. 62/324,039, filed on Apr. 18, 2016.

(51) Int. Cl.
*A61N 5/10*      (2006.01)
*G16H 20/40*   (2018.01)
(Continued)

(52) U.S. Cl.
CPC ......... *A61N 5/1031* (2013.01); *A61N 5/1039* (2013.01); *A61N 5/1045* (2013.01);
(Continued)

(58) Field of Classification Search
CPC .... A61N 5/103; A61N 5/1031; A61N 5/1039; A61N 5/1045; A61N 5/1071;
(Continued)

(56) References Cited

U.S. PATENT DOCUMENTS

2008/0240351 A1   10/2008   Bohsung
2009/0052623 A1   2/2009    Tome

OTHER PUBLICATIONS

Unkelbach, et al: "Paper; The dependence of optimal fractionation schemes on the spatial dose distribution;The dependence of optimal fractionation schemes on the spatial dose distribution", Physics in Medicine and Biology, Institute of Physics Publishing, Bristol GB, vol. 58, No. 1, Dec. 10, 2012.
(Continued)

*Primary Examiner* — Anastasia Midkiff

(57) ABSTRACT

Fractionation optimization receives inputs including a radiation dose distribution to be delivered by fractionated radiation therapy, maximum and minimum number of fractions, and Biologically Effective Dose (BED) constraints for one or more organs-at-risk. A two-dimensional (2D) graph is displayed of a parameter X equal to or proportional to (I) versus a parameter Y equal to or proportional to (II) where N is the number of fractions, D is a total radiation dose to be delivered by the fractionated radiation therapy, and $d_t$ is the fractional dose in fraction t. A constraint BED lines are displayed on the 2D graph depicting each BED constraint. A marker is displayed at a location on the 2D graph defined by a current fractionation and a current total dose. A new value for the current fractionation and/or the current total dose is received, and the marker is updated accordingly. Alternatively a second marker is displayed showing the new frac-
(Continued)

tionation scheme along with its comparative advantages and disadvantages with respect to the current fractionation.

20 Claims, 5 Drawing Sheets

(51) Int. Cl.
  *G16H 15/00*   (2018.01)
  *G16H 40/60*   (2018.01)
  *G16H 30/00*   (2018.01)
  *G06F 3/0484*  (2022.01)
(52) U.S. Cl.
  CPC ........... *A61N 5/1071* (2013.01); *G16H 15/00* (2018.01); *G16H 20/40* (2018.01); *G16H 30/00* (2018.01); *G16H 40/60* (2018.01); *A61N 2005/1074* (2013.01); *A61N 2005/1087* (2013.01); *G06F 3/0484* (2013.01)
(58) Field of Classification Search
  CPC .... A61N 2005/1074; A61N 2005/1087; G06F 3/0484; G16H 10/60; G16H 15/00; G16H 20/40; G16H 30/00; G16H 40/60
  See application file for complete search history.

(56) References Cited

OTHER PUBLICATIONS

Kauweloa, et al: "A graphical user interface (GUI) toolkit for the calculation of three-dimensional (3D) multi phase biological effective dose (BED) distributions including statistical analyses", Computer Methods and Programs in Biomedicine, Elsevier, Amsterdam, NL, vol. 131, Apr. 6, 2016.

Chen et al: "Adaptive fractionation therapy: II. Biological effective dose; Adaptive fractionation II", Physics in Medicine and Biology, Institute of Physics Publishing, Bristol GB, vol. 53, No. 19, Oct. 7, 2008.

Saberian, et al., "A two variable linear program solves the standard linear quadratic formulation of the fractionation problem in cancer radiotherapy", Operations Research Letters, vol. 43 pp. 254-258 (2015).

Fowler, "21 years of Biologically Effective Dose", The British Journal of Radiology, 83 (2010), 554-568.

Saberian, et al., "Optimal fractionation in radiotherapy with multiple normal tissues" 2014.

FRACTIONATION SELECTION TOOL IN RADIOTHERAPY PLANNING

CROSS REFERENCE TO RELATED APPLICATIONS

This application is the U.S. National Phase application under 35 U.S.C. § 371 of International Application No. PCT/EP2017/058477, filed Apr. 10, 2017, published as WO 2017/182300 on Oct. 26, 2017, which claims the benefit of U.S. Provisional Patent Application No. 62/324,039 filed Apr. 18, 2016. These applications are hereby incorporated by reference herein.

FIELD

The following relates generally to the fractionated radiation therapy arts, fractionated radiation therapy planning arts, oncology arts, and related arts.

BACKGROUND

In radiation therapy, a therapeutic dose of radiation is usually delivered to the patient over several radiation therapy sessions with recovery periods of typically one day scheduled between successive fractions. This approach is known as fractionated radiation therapy. The main idea behind fractionated delivery is that the tumor tissue is expected to recover worse from a fraction of dose than healthy tissue, therefore fractionated delivery allows larger total therapeutic dose. Increased dose in more fractions can consequently lead to better tumor control, however, this gain must always be balanced against the probability of normal tissue complications.

Both the positive killing effect of the radiation on the tumor and its negative damaging effect on healthy organs are affected by the fractionation scheme, i.e. the time schedule of dose delivery. These biological effects of fractionation generally depend on tissue type, and the most widely accepted method for investigating them has long been the Biologically Effective Dose (BED) model (see for instance Fowler JF. 21 years of Biologically Effective Dose. *The British Journal of Radiology.* 2010; 83(991):554-568. doi: 10.1259/bjr/31372149.). The BED formalism states that the biological effect of a dose D given in N fractions is:

$$BED = D\left(1 + \frac{D}{N \cdot \alpha/\beta}\right) \quad (0)$$

where the ratio $\alpha/\beta$ is an organ- or tissue-specific parameter characterizing sensitivity of the organ or tissue to fractionation for a certain biological end effect (e.g. cell survival rate). Equation (0) can also be applied to assess the impact of fractionation on the tumor itself, which is characterized by a tumor-specific $\alpha/\beta$ ratio. As can be seen from Equation (0), the same dose D has a smaller effect if given in more fractions (higher N) with a consequently smaller dose per fraction.

The number of fractions N is a design parameter in the planning of fractionated radiation therapy. Since target structures and healthy organs have generally different fractionation sensitivities and receive different dose distributions, the choice of the number of fractions N—and more generally the choice of the fractionation scheme—can have a differential impact on the tumor versus on organs-at-risk (OARs). A well-chosen fractionation could therefore increase the desired therapeutic effect (for example, the necrotizing of the tumor) while limiting undesired damage to OARs. In current clinical practice, however, the fractionation scheme is usually not chosen optimally, hence typically it does not balance the differential effects in an optimal way.

In a typical radiation therapy protocol, a computed tomography (CT), magnetic resonance (MR), or other medical image is acquired and contoured to delineate the tumor and any neighboring OARs. The physician then selects various dose objectives, e.g. the dose to be delivered to the tumor along with constraints on radiation exposure to neighboring OARs. The fractionation scheme is usually also selected at this time. These objectives, as well as the number of fractions N, are usually chosen based on the physician's professional judgment along with consideration of applicable clinical guidelines, taking into account available information such as tumor type, tumor size, and proximity of the tumor to OARs, and perhaps other factors such as patient age, medical condition and patient convenience. Next treatment planning is performed, during which a radiation therapy plan is developed which achieves the dose objectives for the specific anatomy of the patient as represented by the CT or MR image and the drawn tumor and OAR contours. For example, in intensity modulated external radiation therapy (IMRT) the radiation is delivered by a set of radiation beams each modulated by a multi-leaf collimator (MLC), and the radiation therapy planning entails selecting settings for the MLCs such that the set of intensity modulated radiation beams collectively delivers the desired fractional dose distribution for a single fraction of the fractionated radiation therapy, taking into account radiation energy absorption based on an attenuation map generated from the CT or MR image. IMRT planning—and in general, treatment planning—is computationally intensive, involving optimization of typically tens of thousands of parameters to optimize the dose distribution over the voxels (i.e. the small discrete cubic volumes) of a three-dimensional (3D) volume encompassing the tumor and OARs, and may be executed on a server computer, cluster or cloud computing resource, or other high-capacity computer system. The physician reviews the produced plan and makes final approval of the resulting (calculated) dose distribution.

SUMMARY

In one disclosed embodiment, a fractionated radiation therapy planning device comprises a computer including a display component and at least one user input component. At least one non-transitory storage medium stores instructions readable and executable by the computer to perform fractionated radiation therapy planning operations including the following. Fractionation selection inputs are generated or received, including at least a radiation dose distribution to be delivered by the fractionated radiation therapy, a maximum number of fractions $N_{max}$, a minimum number of fractions $N_{min}$, and organ-at-risk (OAR) Biologically Effective Dose (BED) constraints for one or more organs-at-risk. Each OAR BED constraint represents a maximum BED that can be delivered by the fractionated radiation therapy to the corresponding OAR. A two-dimensional (2D) graph is displayed of a parameter X equal to or proportional to $D=\Sigma_{t=1}^{N}d_t$ versus a parameter Y equal to or proportional to $SD=\Sigma_{t=1}^{N}d_t^2$, where N is a number of fractions for delivering the dose distribution, total dose D is a total radiation dose to be delivered by the fractionated radiation therapy, and $d_t$ is the fractional dose of the total radiation dose D to be delivered in the fraction t. OAR BED lines are displayed on the 2D graph that depict each OAR BED constraint. A marker is displayed at a location on the 2D graph defined by a current total dose $D_{curr}$ and a current total squared dose $SD_{curr}$, from which the current number of fractions $N_{curr}$ and the current fractional doses $d_{t,curr}$ are calculated. A new value for at least one of the current total dose $D_{curr}$ and the current total squared dose $SD_{curr}$ is received via the at least one user input component. The displaying of the marker is updated in accord with the updated values of the current total dose $D_{curr}$ and the current total squared dose $SD_{curr}$, furthermore the number of fractions $N_{curr}$ and the fractional doses $d_{t,curr}$ are recalculated and updated to their corresponding new values.

The fractionation selection inputs may further include a target BED for a tumor which is a target BED to be delivered by the fractionated radiation therapy to the tumor, and the fractionated radiation therapy planning operations further include displaying on the 2D graph a target BED line depicting the target BED for the tumor.

One advantage resides in providing more effective leveraging of the fractionation scheme in the planning of radiation therapy.

Another advantage resides in providing improved optimization of treatment parameters in fractionated radiation therapy, such as total prescribed radiation dose, number of fractions, fractional dose values, etc.

Another advantage resides in providing for the foregoing plan adjustments to be made by a physician after the computationally intensive optimization of the radiation therapy plan, without requiring re-optimizing the plan.

Another advantage resides in providing the physician with an intuitive graphical representation of the impact of possible changes in the fractionation and/or of the total prescribed dose on whether the various dose objectives are achieved.

Another advantage resides in providing the physician with such an intuitive graphical representation which also provides visualization of the extent to which a constraint would be violated by a change in fractionation and/or total prescribed dose.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
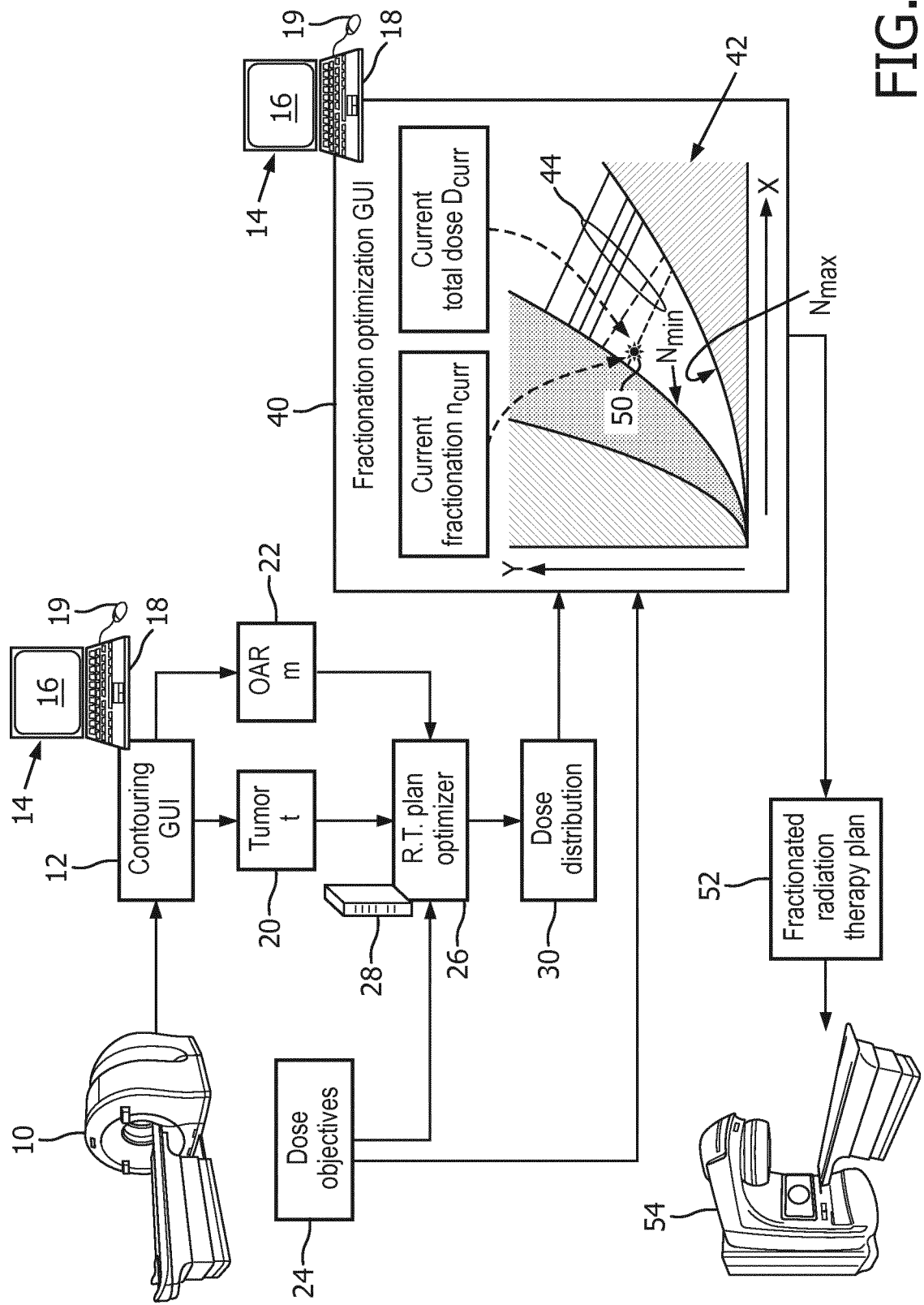
FIG. 1 diagrammatically shows a radiation therapy planning device along with an illustrative radiation therapy delivery device.

With reference to FIG. 1, a radiation therapy planning device or system is described. A medical imaging device 10, such as a computed tomography (CT) or magnetic resonance (MR) scanner, acquires one or more images of the subject including at least the tumor to be irradiated and surrounding tissue possibly including one or more organs-at-risk (OARs). These images are commonly referred to as planning images, as they are used in planning the radiation therapy. To this end a contouring graphical user interface (GUI) 12 implemented on a computer 14 having a display 16 and one or more user input devices (e.g. a keyboard 18 and/or a mouse 19 and/or a touch-sensitive overlay of the display component 16). The contouring GUI 12 enables a skilled user (e.g. a physician, dosimetrist, or so forth) to delineate features in the planning images including the tumor to be irradiated and any OARs in proximity to the tumor (or, more generally, that will be in the path of any therapeutic radiation beam). The contouring can be manual, e.g. employing a mouse pointer to mark the tumor and OAR boundaries), or automatic or semi-automatic, e.g. using a deformable mesh-fitting algorithm to fit meshes to the tumor and OARs. The output of the contouring GUI 12 is a definition of the tumor 20 and (typically) of one or more OARs 22. These definitions may take various forms, e.g. a mesh delineating the tumor/OAR structure and/or a corresponding index map identifying the set of voxels belonging to the tumor/OAR.

The planning images are also typically used to generate a radiation attenuation map to be used for evaluating the absorption of the therapeutic radiation by tissues/organs of the patient. In the case of a CT planning image which is effectively an x-ray absorption map, this entails correcting for differences between x-ray absorption and absorption of the therapeutic radiation (e.g. higher energy x-rays, or accelerated particles such as protons or electrons). In the case of MR images the various tissues are suitably classified by segmenting the regions, e.g. using the contouring GUI 12, and assigning therapeutic radiation absorption values based on tissue type.

The physician also develops a set of dose objectives 24, typically including a minimum (or average, or other objective) therapeutic radiation dose to be delivered to the tumor and a maximum permissible therapeutic radiation dose that can be delivered to each OAR. These constraints on radiation exposure of the OARs may be hard constraints, which must be respected, or soft constraints, which are only desirable. The dose objectives 24 may include other parameters such as tumor margins and/or beam margins to account for various uncertainties. The tumor and OAR definitions 20, 22, together with the dose objectives 24 and the attenuation map generated from the planning images, are inputs to a radiation therapy plan optimizer 26 (for example an intensity modulated radiation therapy (IMRT) or an intensity modulated proton therapy (IMPT) plan optimizer), which optimizes physically realizable parameters such as multi-leaf collimator (MLC) settings for a set of therapeutic radiation beams (which may be physically separate beams or different angular orientations of a therapeutic radiation beam source; moreover, it is contemplated to employ a single radiation beam) to optimize a calculated dose distribution respective to the dose objectives 24. Various known forward or inverse planning techniques can be used depending upon the geometric setup of the radiation beam source(s) and other factors. In some approaches, the plan optimization is initially performed for virtual "beamlets" which are thereafter converted to physically realizable parameters such as MLC settings. The plan optimization is typically computationally intensive, and accordingly the plan optimizer 26 is typically implemented on a suitably powerful computer 28, e.g. a network server, computing cluster, cluster or cloud computing resource, or so forth, although the use of a sufficiently powerful desktop or other personal computer is also contemplated. The output of the radiation plan optimizer 26 is a calculated dose distribution 30 for the patient.

In fractionated radiation therapy employing N radiation therapy sessions (i.e. N fractions), the dose distribution 30 is delivered over N sessions with typically a 1/N fraction of the total dose delivered in each session (assuming equal fractionation; it is also contemplated to employ unequal fractionation in which some radiation delivery sessions deliver a higher proportion of the total dose than others). Conventionally, the number of fractions N, and more generally the fractionation scheme, is chosen by the physician early in the planning process, usually at the time the dose objectives 24 are developed. At this stage, the physician has available information including the contours 20, 22 and the dose objectives, along with various laboratory results such as biopsy results classifying the tumor. Hence, the physician knows the tumor type, size, and its proximity to various OARs. Based on this information the physician conventionally chooses the fractionation scheme based on medical expertise augmented by clinical guidelines, medical literature, comparison with past patients/outcomes, patient convenience, and so forth.

As recognized herein, this approach may not identify the optimal fractionation scheme for a particular patient. As previously noted, in fractionated radiation therapy the Biologically Effective Dose (BED) is different from the physical dose. The BED is typically calculated using the linear-quadratic BED model (Equation (0)). Since the tumor and organs-at-risk have generally different fractionation sensitivities and receive different dose distributions, the choice of fractionation scheme can have a differential impact on the tumor versus OARs, so that the number of fractions N and the total dose D (or in general the fractional doses $d_t$) can be adjusted to increase the desired therapeutic effect tumor and decrease undesired damage to OARs. This, in turn, may enable a reduction in the total physical radiation dose D that is delivered to the patient. In approaches disclosed herein, the total dose D and/or the number of fractions N, and/or the fractional doses $d_t$ can be adjusted to improve the BED delivered to the tumor and OARs. Such adjustments are made after performing the computationally intensive treatment planning (e.g. IMRT or IMPT optimization), and advantageously do not require re-running the plan optimization.

With continuing reference to FIG. 1, a fractionation and total dose adjustment graphical user interface (GUI) 40 is implemented on a computer 14 with a display component 16 and at least one user input component 18, 19 (which may be the same computer 14 on which the contouring GUI 12 is implemented, as in illustrative FIG. 1, or alternatively the contouring GUI and the fractionation and total dose adjustment GUI may be implemented on different computers). The fractionation and total dose adjustment graphical user interface (GUI) 40 displays a two-dimensional (2D) graph 42 of a parameter X equal to the total dose $D=\Sigma_{t=1}^{N} d_t$ versus a parameter Y equal to the total squared dose $SD=\Sigma_{t=1}^{N} d_t^2$, where N is a number of fractions for delivering the dose distribution 30, total dose D is a total radiation dose to be delivered by the fractionated radiation therapy, and $d_t$ is a fractional dose of the total radiation dose D to be delivered in the fraction t. Again, in the illustrative examples X is equal to $D=\Sigma_{t=1}^{N} d_t$ and Y is equal to $SD=\Sigma_{t=1}^{N} d_t^2$, more generally these can be proportionalities, i.e. X is proportional to $D=\Sigma_{t=1}^{N} d_t$ and Y is proportional to $SD=\Sigma_{t=1}^{N} d_t^2$. In the illustrative embodiments X is the abscissa and Y is the ordinate of the 2D graph 42, but these may optionally be reversed. The 2D graph 42 is of a general type described in Saberian et al., "A two-variable linear program solves the standard linear-quadratic formulation of the fractionation problem in cancer radiotherapy", Operations Research Letters, vol. 43 pages 254-258 (2015). However, the 2D graph 42 has a number of features that cooperate to provide a GUI that is effective to enable the medical professional to adjust the fractionation and/or total dose in a principled way to provide improved radiation therapy efficacy.

The 2D graph 42 includes display of parabolic boundary curves indicating the maximum number of fractions $N_{max}$ and the minimum number of fractions $N_{min}$, assuming equal fractional doses (i.e. $d_t$=constant). More generally, a given number of fractions N with equal fractional doses will correspond to a parabolic curve on the 2D graph 42, and for fraction number values in the inclusive range of $[N_{min}, N_{max}]$ the parabolic curves representing uniform fractionation schemes will lie in an operational region that is bounded by the parabolic boundary curves indicating the maximum number of fractions $N_{max}$ and the minimum number of fractions $N_{min}$. Since the number of fractions N is a whole number, optionally the 2D graph has a discretization grid (not shown) comprising the set of parabolic curves defined by the set of integers in the inclusive range $[N_{min}, N_{max}]$ assuming equal fractional doses.

A further feature is the display of iso-BED lines 44 to represent constraints on the upper limit of BED that the various OARs should receive, and/or to represent the tumor target BED. Because of the linear-quadratic form of the BED model (Equation (0)), these iso-BED lines 44 are straight lines on the 2D graph 42. Optionally, the iso-BED lines 44 may be drawn only in the operational region between the $[N_{min}, N_{max}]$ parabolic curve boundaries. Furthermore, a marker 50 is displayed at a location on the 2D graph 42 defined by the current total dose $D_{curr}$ and the current total squared dose $SD_{curr}$, which determine the current number of fractions $N_{curr}$ and the current fractional doses $d_{t,curr}$. By moving this marker 50, the user can adjust the current total dose $D_{curr}$ and the current total squared dose $SD_{curr}$, thereby adjusting the current number of fractions $N_{curr}$ and the current fractional doses $d_{t,curr}$ as well, and can immediately see this adjustment in the context of the iso-BED lines 44 representing the tumor target BED and the various OAR upper BED constraints. In this way, the user can select final values for the fractionation and total dose. When the user indicates that the current total dose $D_{curr}$ and the current total squared dose $SD_{curr}$ are final, the final value for the number of fractions and the fractional doses are set to the corresponding current fraction number $N_{curr}$ and the current fractional dose $d_{t,curr}$. Note that this processing does not alter the dose distribution 30 except to the extent that the dose distribution 30 is scaled uniformly upward or downward in amplitude by the current total dose $D_{curr}$—but the shape of the dose distribution 30 is unaltered, and there is no need to re-run the plan optimizer 26. The resulting fractionated radiation therapy plan 52 includes the dose distribution 30 (or corresponding physically realizable parameters such as MLC settings), the final fractionation, and the final per-fraction radiation dose $d_t$ (corresponding to a physically realizable parameter such as beam attenuator setting).

The fractionated radiation therapy plan 52 is executed in N radiation therapy sessions by a radiation therapy delivery device 54, such as a linear accelerator (linac), proton beam source, or so forth. Moreover, in alternative embodiments it is contemplated for the radiation therapy to be delivered as brachytherapy by way of implantation of radioactive seeds in a pattern designed to implement the optimized dose distribution 30. In this case the N fractions correspond to N different brachytherapy seed implantation sessions.

In the following, a detailed example of implementation of the fractionation and total dose adjustment GUI 40 is described. The skilled artisan can readily implement this example as programming code for programming a computer to implement the fractionation and total dose adjustment GUI 40. The following notation is used:

$n^T$: Number of voxels in the tumor(s).

$\mathcal{N}^T = \{1, \ldots, n^T\}$: Index set of voxels in the tumor(s).

$A^T \in \mathbb{R}^{n^T \times k}$: Tumor dose matrix $u \in \mathbb{R}^k$: Vector of beam weights.

$\alpha/\beta^T$: The $\alpha/\beta$ ratio of the tumor.

$\mathcal{M} = \{1, \ldots, M\}$: Index set of organ at risk (OAR) constraints.

$\mathcal{N}^m = \{1, \ldots, n^m\}$: Index set of voxels in the OAR corresponding to constraint $m \in \mathcal{M}$.

$A^m \in \mathbb{R}^{n^m \times k}$: Dose matrix for the OAR consisting of $n^m$ voxels corresponding to constraint $m \in \mathcal{M}$.

$\alpha/\beta^m$: the $\alpha/\beta$ ratio of the OAR corresponding to constraint m.

$N \in \mathbb{N}$: Number of fractions $d \in \mathbb{N}^N$: Vector of average tumor doses in the N fractions.

$v_i$ and $[v]_i$: The i-th element of vector v.

The dose distribution can be described in this notation is as follows. In the nominal plan with beam weights $u_{nominal}$ the total average tumor dose is:

$$D^T = \frac{1}{n^T} \sum_{i=1}^{n^T} [A^T \cdot u_{nominal}]_i$$

This dose is received in N fractions, where in each fraction $d_t$ dose is delivered to the tumor, i.e. $D^T = \sum_{t=1}^N d_t$. The dose sparing factor for a voxel $j \in \mathcal{N}^m$ in an OAR corresponding to constraint m is therefore:

$$s_j^m = \frac{[A^m \cdot u_{nominal}]_j}{D^T}$$

The dose received in this voxel in fraction t is:

$$s_j^m \cdot d_t = [A^m \cdot u_{nominal}]_j \frac{d_t}{D^T}$$

For the tumor voxels we can similarly define dose sparing factors as:

$$s_j^T = \frac{[A^T \cdot u_{nominal}]_j}{D^T}$$

and can write the dose received in fraction t as:

$$s_j^T d_t = [A^T \cdot u_{nominal}]_j \frac{d_t}{D^T}$$

For the nominal treatment the BED in the tumor voxels is given by:

$$BED_j^T = \sum_{t=1}^N s_j^T d_t + \rho^T \sum_{t=1}^N (s_j^T d_t)^2 = s_j^T \sum_{t=1}^N d_t + \rho^T (s_j^T)^2 \sum_{t=1}^N d_t^2 \quad (1)$$

where $\rho^T = 1/(\alpha/\beta^T)$ was introduced. We similarly introduce $\rho^m = 1/(\alpha/\beta^m)$, which results in a basically identical formula for the BED in voxel $j \in \mathbb{R}^m$ for the OAR corresponding to constraints m:

$$BED_j^m = \sum_{t=1}^N s_j^m d_t + \rho^m \sum_{t=1}^N (s_j^m d_t)^2 = s_j^m \sum_{t=1}^N d_t + \rho^m (s_j^m)^2 \sum_{t=1}^N d_t^2 \quad (2)$$

It is desired to find the optimal fractionation scheme that maximizes the tumor dose and respects the tolerances on the OARs. Therefore we first investigate how the objective function and the constraints of this optimization problem can be formulated in terms of BED. To this end, the different constraint types associated to OARs and their corresponding BED formulation are considered.

Let us assume that constraints $m \in \mathcal{M}_1$ ($\mathcal{M}_1 \subset \mathcal{M}$) state that a maximum dose of $D_{max}^m$ is tolerated by the corresponding OAR if given in $N^m$ fractions. This is equivalent to a BED of:

$$BED(D_{max}^m, N^m) = BED_{max}^m = D_{max}^m \left(1 + \rho^m \frac{D_{max}^m}{N^m}\right)$$

and hence the BED constraint on voxels $j \in \mathbb{R}^m$ is:

$$BED_j^m = s_j^m \sum_{t=1}^N d_t + \rho^m (s_j^m)^2 \sum_{t=1}^N d_t^2 < BED_{max}^m \forall j \in \mathcal{N}^m$$

Since the $s_j^m$ dose sparing factors do not depend on the fractionation it is satisfactory to simply enforce the constraint on the voxel receiving the highest dose. Introducing $$\sigma^m = \max_{j \in \mathcal{N}^m} s_j^m$$

as a generalized dose sparing factor and $B^m = BED_{max}^m$ as a generalized BED tolerance, the final form of the maximum dose constraints is:

$$\sigma^m \sum_{t=1}^N d_t + \rho^m (\sigma^m)^2 \sum_{t=1}^N d_t^2 < B^m \forall m \in \mathcal{M}_1 \quad (3)$$

A maximum dose volume histogram (DVH) constraint can be formulated as follows. Let us assume that constraints $m \in \mathcal{M}_2$ ($\mathcal{M}_2 \subset \mathcal{M}$) state that no more than $F^m$ fraction of the corresponding OAR volume can receive a dose higher than $D_{dv}^m$ if given in $N^m$ fractions. This is equivalent to a BED of:

$$BED(D_{dv}^m, N^m) = D_{dv}^m \left(1 + \rho^m \frac{D_{dv}^m}{N^m}\right)$$

By defining an indicator function $f_j^m(d, N)$ for each voxel $j \in \mathbb{R}^m$ as:

$$f_j^m(d, N) = \begin{cases} 1 & \text{if } BED_j^m > BED(D_{dv}^m, N^m) \\ 0 & \text{otherwise} \end{cases},$$

the BED constraint can be formulated in the following way:

$$\sum_{j=1}^{n^m} f_j^m(d, N) < \lfloor F^m n^m \rfloor$$

where $\lfloor \alpha \rfloor$ stands for the floor function, i.e. the biggest integer smaller than a. Since the dose sparing factors appearing in the definition of $f_j^m(d, N)$ (through the $BED_j^m$ term defined by Equation (2)) do not depend on the fractionation scheme, we can reformulate the constraint similarly to the maximum point dose case. What we need is at least $n^m - \lfloor F^m n^m \rfloor$ number of voxels for which $BED_j^m \leq BED(D_{dv}^m, N^m)$ holds, which we can ensure by enforcing the BED constraint on the voxel having the $(n^m - \lfloor F^m n^m \rfloor)$th smallest dose sparing factor. If we order the dose sparing factors in an ascending series and denote it by $s_j^{m,\uparrow}$ (i.e. where $\forall j \in \mathbb{R}^m \exists l: s_j^{m,\uparrow} = s_l^m \land s_l^{m,\uparrow} \geq s_l^{m,\uparrow} \forall l > j$), we need to pick the voxel corresponding to the $(n^m - \lfloor F^m n^m \rfloor)$th value. Assigning the generalized dose sparing factor and BED tolerance as $$\sigma^m = s_{n^m - \lfloor F^m n^m \rfloor}^{m,\uparrow}$$

and $B^m = BED(D_{dv}^m, N^m)$, the final BED constraint is:

$$\sigma^m \sum_{t=1}^{N} d_t + \rho^m (\sigma^m)^2 \sum_{t=1}^{N} d_t^2 < B^m \forall m \in \mathcal{M}_2 \quad (4)$$

A maximum absolute dose volume histogram constraint can be formulated as follows. Let us assume that constraints $m \in \mathcal{M}_3$ ($\mathcal{M}_3 \subset \mathcal{M}$) state that no more than a $V^m$ absolute volume of the corresponding OAR can receive a dose higher than $D_{adv}^m$ if given in $N^m$ fractions. Denoting the total volume of the OAR by $V_{tot}^m$, the constraint is equivalent to the maximum DVH case described above, with $F^m = V^m/V_{tot}^m$.

A maximum critical absolute dose volume constraint can be formulated as follows. Let us assume that constraints $m \in \mathcal{M}_4$ ($\mathcal{M}_4 \subset \mathcal{M}_3$) state that at least $V^m$ absolute volume of the corresponding OAR has to receive a dose lower than $D_{cadv}^m$ a if given in $N^m$ fractions. With $F^m = (V_{tot}^m - V^m)/V_{tot}^m$ this is again equivalent to the maximum DVH case.

A maximum mean dose constraint can be formulated as follows. First consider the relation between the mean physical dose and the mean BED. Suppose that in a plan the voxel doses in an organ are $D_j = s_j D^{ref}$ ($j = 1, \ldots, n$), where $s_j$ are the dose sparing factors for some $D^{ref}$ reference dose given in N fractions with $d_t^{ref}$ dose per fraction values (i.e. $D^{ref} = \sum_{t=1}^{N} d_t^{ref}$). The mean physical dose in this organ is $$D_{mean} = \frac{1}{n}\sum_{j=1}^{n} D_j = \frac{1}{n}\sum_{j=1}^{n} s_j \sum_{t=1}^{N} d_t^{ref}.$$

The corresponding mean BED is:

$$BED_{mean} = \frac{1}{n}\sum_{j=1}^{n} BED_j(d^{ref}, N) = \frac{1}{n}\sum_{j=1}^{n}\left(s_j \sum_{t=1}^{N} d_t^{ref} + \rho \sum_{t=1}^{N} (s_j d_t^{ref})^2\right) \quad (5)$$

$$= D_{mean}\left(1 + \rho \frac{\frac{1}{n}\sum_{j=1}^{n}(s_j)^2 \sum_{t=1}^{N}(d_t^{ref})^2}{\frac{1}{n}\sum_{j=1}^{n} s_j \sum_{t=1}^{N} d_t^{ref}}\right)$$

$$= D_{mean}\left(1 + \rho \frac{D_{mean}}{N} \frac{n\sum_{j=1}^{n}(s_j)^2}{\left(\sum_{j=1}^{n} s_j\right)^2} \frac{N\sum_{t=1}^{N}(d_t^{ref})^2}{\left(\sum_{t=1}^{N} d_t^{ref}\right)^2}\right)$$

$$= D_{mean}\left(1 + \rho \frac{D_{mean}}{N} \frac{nq}{(p)^2}\varphi_t\right)$$

$$= D_{mean}\left(1 + \rho \frac{D_{mean}}{N}\varphi \varphi_t^{ref}\right)$$

where we introduced $p = \sum_{j=1}^{n} s_j$, $q = \sum_{j=1}^{n}(s_j)^2$ the dose shape factor $$\varphi = \frac{nq}{(p)^2}$$

and the fractionation modifying factor $$\varphi_t^{ref} = \frac{N\sum_{t=1}^{N}(d_t^{ref})^2}{\left(\sum_{t=1}^{N} d_t^{ref}\right)^2}.$$

The dose shape and the fractionation modifying factors take into account the effects of non-uniformity in the dose distribution and the fractionation. By definition $\varphi > 1$ and $\varphi_t^{ref} > 1$ hold, which have the following consequences. First, Non-uniformity in the dose distribution ($\varphi$) and the fractionation ($\varphi_t^{ref}$) both increase the mean BED. Second, the mean BED is always higher than or equal to the BED equivalent of the mean physical dose, as in the latter it is assumed that the dose distribution is uniform (i.e. $\varphi = 1$). Therefore for uniform fractionation ($\varphi_t^{ref} = 1$) the following holds:

$$BED(D_{mean}, N) = D_{mean}\left(1 + \rho \frac{D_{mean}}{N}\right) \leq BED_{mean}$$
$$= D_{mean}\left(1 + \rho \frac{D_{mean}}{N}\varphi\right)$$

A third consequence is that two dose distributions with identical mean physical doses ($D_{mean}^1 = D_{mean}^2$) and fractionation schemes ($\varphi_t^{ref,1} = \varphi_t^{ref,2}$) are not necessarily iso-effective in terms of mean BED. $BED_{mean}^1 = BED_{mean}^2$ only holds if the spatial distributions are similar too (i.e. $\varphi^1 = \varphi^2$ is true).

Mean BED constraints are considered next. Let us now assume that constraints $m \in \mathcal{M}_5$ ($\mathcal{M}_5 \subset \mathcal{M}$) state that a maximum mean dose of $D_{mean}^m$ is tolerated by the corresponding OAR if given in $N^m$ fractions. This is equivalent to a BED of:

$$BED(D_{mean}^m, N^m) = D_{mean}^m \left(1 + \rho^m \frac{D_{mean}^m}{N^m}\right) \qquad (6)$$

Further assuming that this tolerance was derived in a plan with a dose shape factor of $\varphi^{m,ref}$ the tolerated mean BED is:

$$BED_{mean}^m = D_{mean}^m \left(1 + \rho^m \frac{D_{mean}^m}{N^m} \varphi^{m,ref}\right) \qquad (7)$$

The BED constraint can therefore be formulated as follows:

$$\frac{1}{n^m} \sum_{j=1}^{n^m} \left( s_j^m \sum_{t=1}^{N} d_t + \rho^m (s_j^m)^2 \sum_{t=1}^{N} d_t^2 \right) < BED_{mean}^m \qquad (8)$$

Introducing $p^m = \sum_{j=1}^{n^m} s_j^m$, $q^m = \sum_{j=1}^{n^m} (s_j^m)^2$ and $\varphi^m = n^m q^m / (p^m)^2$ characterizing the dose distribution in the plan, the generalized dose sparing factor and the generalized BED tolerance can be defined as $\sigma^m = q^m/p^m$ and $B^m = \varphi^m BED_{mean}^m$. The constraint given by Equation (8) can therefore be formulated in a similar fashion to Equation (3), i.e. as:

$$\sigma^m \sum_{t=1}^{N} d_t + \rho^m (\sigma^m)^2 \sum_{t=1}^{N} d_t^2 < B^m \quad \forall m \in \mathcal{M}_5 \qquad (9)$$

Since the $\varphi^{m,ref}$ dose shape factors for the tolerance dose values are practically never known, in the following we will always assume that $\varphi^m \leq \varphi^{m,ref} \forall m \in \mathcal{M}_5$ holds. Correspondingly the mean dose constraint is:

$$\sigma^m \sum_{t=1}^{N} d_t + \rho^m (\sigma^m)^2 \sum_{t=1}^{N} d_t^2 < B^m \quad \forall m \in \mathcal{M}_5 \qquad (10)$$

with $p^m = \sum_{j=1}^{n^m} s_j^m$, $q^m = \sum_{j=1}^{n^m} (s_j^m)^2$, the generalized dose sparing and shape factors being $\sigma^m = q^m/p^m$ and $\varphi^m = n^m q^m / (p^m)^2$ respectively, and $$B^m = \varphi^m D_{mean}^m \left(1 + \rho^m \frac{D_{mean}^m}{N^m} \varphi^m\right)$$

being the generalized BED constraint.

For all the foregoing illustrative constraint examples, it was assumed that there is a single dose (and optionally volume) value for a given fractionation scheme that defines the tolerance. This allowed the constraints to be formulated as the BED equivalent of dose tolerance (with the help of the dose shape factor in case of the mean constraints). In practice however, in situations where multiple fractionation schemes are considered physicians often have separate sets of constraints for the different fraction numbers. This means that constraint $m \in \mathcal{M}$ states that $D_i^m$ dose is tolerated by the corresponding OAR if given in $N_i^m$ fractions, and there are $C^m$ different fractionation schemes for which tolerance data is given ($i = \{1, \ldots, C^m\}$). While in theory these tolerances should be iso-effective, they are most often not BED equivalent, i.e.:

$$D_i^m \left(1 + \rho^m \frac{D_i^m}{N_i^m}\right) = \text{constant} \quad \forall i = \{1, \ldots, C^m\} \qquad (11)$$

does not hold. This results in BED tolerances that depend on the number of fractions. From the optimization point of view this is manageable, however it is contradictory to the concept of Biologically Effective Dose making different fractionation schemes iso-effective.

Therefore in illustrative embodiments herein, two restrictions are placed on the allowed dose constraints. First, for any constraint $m \in \mathcal{M}$ tolerance doses can be given for at most $C^m = 2$ different fractionation schemes. The reasoning behind this is that two dose values ($D_1^m$ and $D_2^m$) given in distinct fraction numbers ($N_1^m$ and $N_2^m$) can always be made BED equivalent, since $$D_1^m \left(1 + \frac{D_1^m}{N_1^m \alpha/\beta_{eq}^m} \varphi^m\right) = D_2^m \left(1 + \frac{D_2^m}{N_2^m \alpha/\beta_{eq}^m} \varphi^m\right)$$

can always be satisfied with an $\alpha/\beta_{eq}^m$ ratio of:

$$\alpha/\beta_{eq}^m = \varphi^m \frac{(D_1^m)^2/N_1^m - (D_2^m)^2/N_2^m}{D_2^m - D_1^m} \qquad (12)$$

($\varphi^m = 1$ for all constraints other than the mean in Equation (12)). Therefore in the constraint equations (Equations (3), (4), and (11)) one can use $\rho^m = 1/\alpha/\beta_{eq}^m$ and calculate the $B^m$ generalized BED tolerance from either of the two $D_i^m$, $N_i$ pairs.

Second, for all constraints only such dose value/fraction number pairs are allowed which can be made BED equivalent with a positive $\alpha/\beta$ value. Although Equation (12) ensures that the two schemes have the same BED, this value is not necessarily positive. For example $D_1 = 25$ in $N_1 = 5$ fractions and $D_2 = 45$ in $N_2 = 15$ fractions are only BED equivalent with $\alpha/\beta_{eq} = -0.5$, at a BED value of $$D_1 \left(1 + \frac{D_1}{N_1 \alpha/\beta_{eq}}\right) = D_2 \left(1 + \frac{D_2}{N_2 \alpha/\beta_{eq}}\right) = -225_{-0.5}.$$

Such unphysical situations highlight a limit of the Linear-Quadratic model based BED. It is also worth noting that whenever the equivalent $\alpha/\beta$ value is negative, it is also highly sensitive to the dose values $D_1$ and $D_2$, therefore typically small ($\approx 5\%$) adjustments of these lead to positive $\alpha/\beta_{eq}$ values.

The foregoing two restrictions limit applicability; however, even with these limitations the formulation effectively fits current clinical practice, where most often only a limited range of fractionation schemes is considered. A physician might chose for example between $N_1 = 5$ and $N_2 = 15$ fractions (and correspondingly may have a different set of constraints for the two schemes), but will almost never consider all number of fractions between $N_1 = 1$ and $N_2 = 45$. Furthermore it is reasonable to assume that the two constraint sets are interpreted as iso-effective, therefore taking them into account with an $\alpha/\beta_{eq}$ value making them BED equivalent typically follows the physician's original intent.

The optimization of the tumor dose is next considered. Since we are aiming to maximize the tumor dose the objective function of the optimization problem is based on the tumor BED. In the following, three different approaches are considered as illustrative examples: optimizing the minimum and the mean tumor BED, as well as optimizing the BED equivalent of the average tumor dose.

Minimum dose optimization can be formulated as follows. In this approach the dose in the "coldest spot" of the tumor is maximized, i.e. maximize the BED in the voxel having the smallest BED. Since BED is monotone in the dose and we are only optimizing the fractionation scheme, this is equivalent to maximizing the BED in the voxel with the lowest dose "sparing" factor in the tumor. Introducing $$\sigma^T = \min_{j \in \mathcal{N}^T} s_j^T$$

the objective function to maximize is:

$$BED_{min}^T = \min_{j \in \mathcal{N}^T} s_j^T \sum_{t=1}^N d_t + \rho^T (s_j^T)^2 \sum_{t=1}^N d_t^2 = \sigma^T \sum_{t=1}^N d_t + \rho^T (\sigma^T)^2 \sum_{t=1}^N d_t^2 \quad (13)$$

Mean dose optimization can be formulated as follows. The mean tumor BED can be calculated the same way as the mean BED in the OARs. Using the s dose "sparing" factors for the tumor voxels $j \in \mathcal{M}^T$ we can define $p^T = \sum_{j=1}^{n^T} = s_j^T$, $q^T = \sum_{j=1}^{n^T} (s_j^T)^2$, $\sigma^T = q^T/p^T$ and $\varphi^T = n^T q^T/(p^T)^2$, with which the mean tumor BED can be written as:

$$BED_{mean}^T = \frac{1}{\varphi^T}\left(\sigma^T \sum_{t=1}^N d_t + \rho^T (\sigma^T)^2 \sum_{t=1}^N d_t^2\right) \quad (14)$$

The dose shape factor $\varphi^T$ does not depend on the fractionation scheme, therefore can be omitted from the objective function.

Uniform dose optimization can be formulated as follows. Assuming that the dose in the tumor is uniform the mean tumor BED is given by:

$$BED_{uniform}^T = \sum_{t=1}^N d_t + \rho^T \sum_{t=1}^N d_t^2 \quad (15)$$

Defining $\sigma^T=1$, Equation (15) can be written in a form similar to Equations (13) and (14) as:

$$BED_{uniform}^T = \sigma^T \sum_{t=1}^N d_t + \rho^T (\sigma^T)^2 \sum_{t=1}^N d_t^2 \quad (16)$$

Having provided some illustrative constraint and tumor dose formulations, the optimization problem to be solved is next considered. Using the OAR constraints defined by Equations (3), (4), and (11) together with the $\alpha/\beta$ ratios given by Equation (12) where applicable and the tumor BED given by Equation (13), (14), or (16), the BED based optimization problem can be formulated as follows:

$$\max_{N,d} BED^T = \max_{N,d} \sigma^T \sum_{t=1}^N d_t + \rho^T (\sigma^T)^2 \sum_{t=1}^N d_t^2 \quad (17)$$

subject to the following constraints:

$$\sigma^m \sum_{t=1}^N d_t + \rho^m (\sigma^m)^2 \sum_{t=1}^N d_t^2 \leq B^m \quad \forall m \in \mathcal{M} \quad (18)$$

$$d_t \geq 0 \quad \forall t = 1, \ldots, N \quad (19)$$

$$N_{min} \leq N \leq N_{max}. \quad (20)$$

Introducing the total dose $X = \sum_{t=1}^N d_t$ and the total squared dose $Y = \sum_{t=1}^N d_t^2$, Equations (17) and (18) can be rewritten as:

$$\max_{d,N} \sigma^T X + \rho^T (\sigma^T)^2 Y \quad (21)$$

subject to:

$$\sigma^m X + \rho^m (\sigma^m)^2 Y \leq B^m \quad \forall m \in \mathcal{M} \quad (22)$$

$$X = \sum_{t=1}^N d_t, \quad Y = \sum_{t=1}^N d_t^2 \quad (23)$$

$$X \geq 0, \quad Y \geq 0, \quad d_t \geq 0 \quad \forall t = 1, \ldots, N \quad (24)$$

$$\sqrt{Y} \leq X \leq \sqrt{NY} \quad (25)$$

$$N_{min} \leq N \leq N_{max} \quad (26)$$

The constraint given by Equation (25) is a consequence of the definitions of X and Y (Equation (23)) whereas Equation (26) represents practical limits on the number of fractions N.

Figure 2:
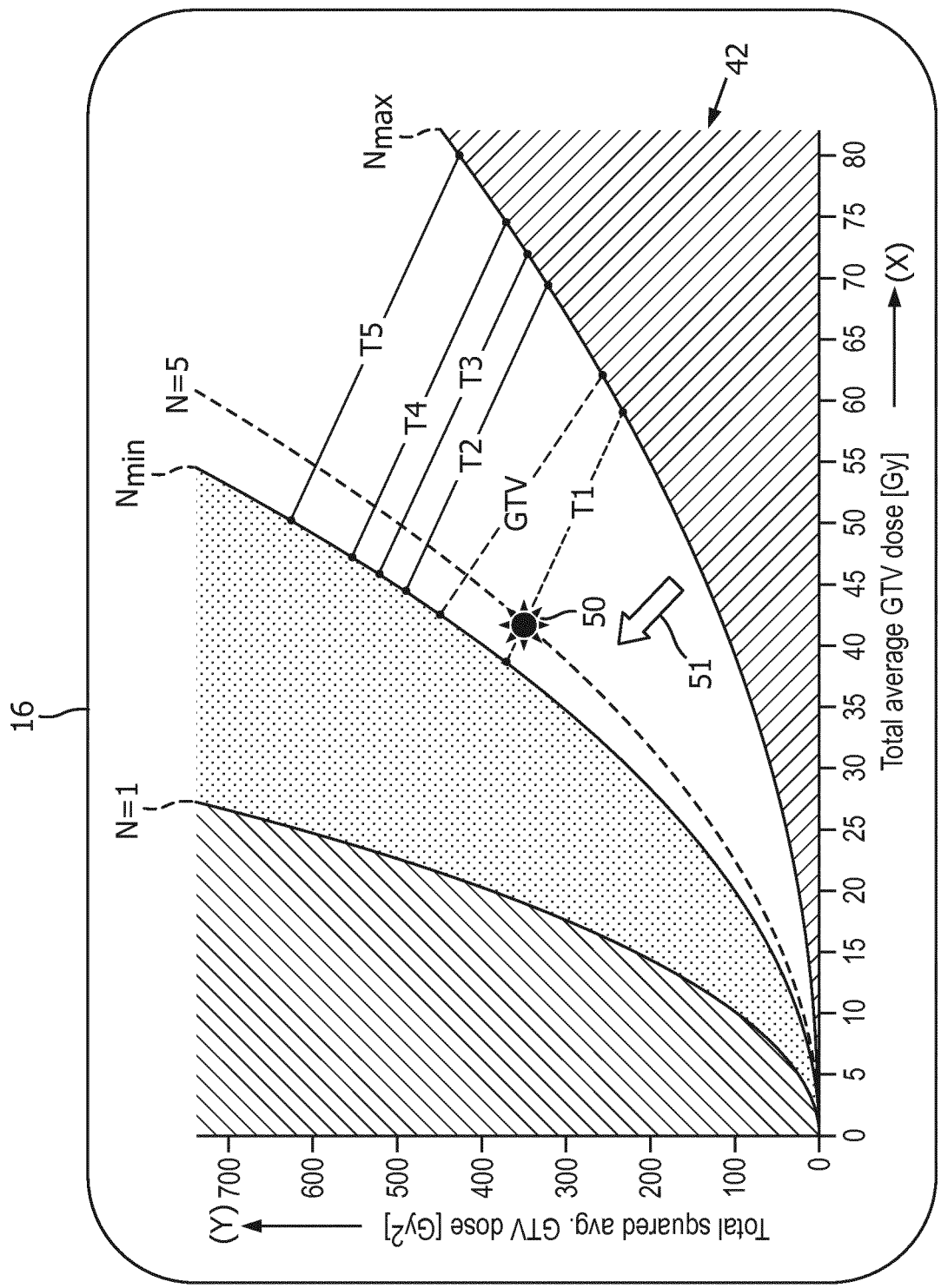
FIGS. 2-5 diagrammatically show examples of the display of the fractionation optimization graphical user interface (GUI) of FIG. 1.

With continuing reference to FIG. 1 and with further reference to FIG. 2, in the optimization problem Equations (24)-(26) define the feasible region in terms of the total dose (X) and the total squared dose (Y). This region can conveniently be visualized on the X-Y plane as the 2D graph 42, which is shown in enlarged view in FIG. 2. The following considerations apply.

Since $N \geq 1$ and $X \leq \sqrt{NY}$ (Equation (25)), $Y > X^2$ defines a parabolic limit labeled N=1 in FIG. 2, which is always infeasible (only one fraction is given, the Y total squared dose value cannot be larger than the square of the X dose given in that single fraction).

Similarly, since $N \leq N_{max}$, $Y < X^2/N_{max}$ defines another parabolic limit labeled $N_{max}$ in FIG. 1, which is also infeasible (area below the $N_{max}$ curve): the minimum total squared dose value is reached when the fraction doses are equal, for a given X total dose and fixed $N_{max}$ number of fractions $X^2/N_{max}$ is this minimum value.

For any given fraction number N, $Y < X^2/N$ is always infeasible. However this does not mean that the region above the $Y = X^2/N_{min}$ line (labeled as $N_{min}$ in FIG. 2) would be infeasible as well. Any (X, Y) point for which Equation (25) holds, i.e. for which $Y \leq X^2$ and $Y \geq X^2/N$ represents a valid N fraction treatment: in the extreme case almost the total dose can be given in 1 fraction with practically zero doses in the other N−1 fractions, in essence representing a single fraction schedule as an N fraction treatment. The importance of having the lower limit $N_{min}$ on the number of fractions is exactly to avoid such situations.

One practical approach for the above problem is to limit the allowed dose per fraction values to two distinct figures, i.e. to impose a further constraint as:

$$d_t \in \{d_{high}, d_{low}\} \forall t=1,\ldots,N \quad (27)$$

The choice may seem to be limiting, however it can be shown that even with only allowing two distinct dose values any feasible (X, Y) point satisfying Equation (25) remain feasible, therefore optimality is not lost. Furthermore by allowing $N_{low}$ number of low dose fractions in an N fraction treatment the corresponding (X, Y) points are all in the region defined by $X^2/N \leq Y \leq X^2/(N-N_{low})$, therefore between the lines of equal dose per fraction treatments with N and $N-N_{low}$ number of fractions.

With the constraint given by Equation (27) it is possible to have a practical upper limit for the feasible region: allowing at most $N_{low}$ number of low dose fractions $Y > X^2/(N_{min}-N_{low})$ becomes infeasible (area above the $N_{min}$ parabola in FIG. 2).

With the above limitations the practical feasible region of the fractionation problem is $X^2/N_{max} \leq Y \leq X^2/(N_{min}-N_{low})$, that is, the area between the parabolas labeled $N_{min}$ and $N_{max}$ in FIG. 2.

Taking into account these practical considerations the final form of the optimization problem that has to be solved is:

$$\max_{d,N} \sigma^T X + \rho^T (\sigma^T)^2 Y \quad (28)$$

$$\text{subject to } \sigma^m X + \rho^m (\sigma^m)^2 Y \leq B^m \;\forall m \in \mathcal{M} \quad (29)$$

$$X = \sum_{t=1}^{N} d_t, \; Y = \sum_{t=1}^{N} d_t^2 \quad (30)$$

$$d_t \geq 0 \;\forall t = 1,\ldots,N \quad (31)$$

$$0 \leq N_{low} < N_{min} \leq N \leq N_{max} \quad (32)$$

$$\frac{X^2}{N_{max}} \leq Y \leq \frac{X^2}{N_{min} - N_{low}} \quad (33)$$

Inputs to the optimization problem include the dose distribution (so that the generalized dose sparing factors $\sigma^T$ and $\sigma^m$, as well as the dose shape factors appearing in $B^m$ can be calculated), the dose constraints (for obtaining the $B^m$ generalized BED constraints), and the limits on the considered fractionation schemes ($N_{min}$, $N_{max}$ and $N_{low}$). The solution provides the optimal total dose X and total squared dose Y, as well as a fractionation scheme in terms of $d_{high}$ and $d_{low}$ achieving these values.

Since both the objective function and the OAR constraints are linear in the total dose and the total squared dose, furthermore the constraints coming from the limited number of allowed fractions are second order polynomials, the problem has a convenient graphical representation on the 2D graph 42. The constraint given in Equation (29) can be reformulated as:

$$Y \leq \frac{B^m}{\rho^m (\sigma^m)^2} - \frac{1}{\rho^m \sigma^m} X \;\forall m \in \mathcal{M}$$

With reference again to FIG. 2, this combined with Equation (33) give the final feasible region on the X-Y plane: the two parabolas represent the shortest hypofractionation (basically with $N_{min}-N_{low}$ fractions) and longest hyperfractionation (with $N=N_{max}$ fractions) cases that are allowed, whereas the straight lines (each with an abscissa of $B^m/\sigma^m$ and an ordinate of $B^m/\rho^m (\sigma^m)^2$) mark the boundary of the safe fractionation schemes.

Since the number of low dose fractions ($N_{low}$) does not significantly impact the analysis, in the following the low dose fractions are generally neglected by simply assuming $N_{low}=1$. Similarly, the term "minimum number of fractions" or the like should be interpreted with the understanding that one of those can have a lower (possibly zero) fractional dose than the others, effectively making the minimum number of fractions $N_{min}-1$. This technicality is introduced in order to conform to a physician's actual intent with having a lower limit on the number of fractions; to best approach current clinical practice of having equal fractional doses; and to enable realizing any feasible point of the X-Y plane, not only the ones corresponding to the parabolas representing uniform fractionation schemes. In general therefore, the minimum fractions $N_{min}$ in examples described herein assumes a single low dose fraction $N_{low}=1$ except where explicitly indicated otherwise.

Furthermore, in implementing the fractional optimization GUI 40 it is generally assumed that the fractional doses $d_t$ of the total radiation dose D to be delivered in each fraction t other than the low dose fraction are the same and are equal to $d_{high}$ given later, whereas the low dose fractional dose is equal to $d_{low}$, although neither of these assumptions are required.

In illustrative FIG. 2, the BED lines of this example include five possible BED constraints for a liver, denoted by five tolerances T1 . . . T5 where T1 is the strictest tolerance (lowest permissible dose to the liver) and T5 is the loosest tolerance (highest permissible dose to the liver). A target BED for a tumor is also shown, labeled as GTV (standing for Gross Target Volume).

In general, the target BED line depicting the target BED for the tumor is given by $\sigma^T X + \rho^T (\sigma^T)^2 Y = B^T$ where $B^T$ is the target BED to be delivered by the fractionated radiation therapy to the tumor, $\sigma^T$ is a constant, and $\rho^T$ is the inverse of the $\alpha/\beta$ ratio of the tumor in a linear-quadratic BED model. Suitable values for the parameters $\sigma^T$ and $\rho^T$ have been described previously. In similar fashion, the constraint BED line depicting BED constraint m is given by $\sigma^m X + \rho^m (\sigma^m)^2 Y = B^m$ where $B^m$ is the upper constraint on the BED to be delivered by the fractionated radiation therapy to the corresponding organ at risk, $\sigma^m$ is a constant, and $\rho^m$ is the inverse of the $\alpha/\beta$ ratio of the corresponding organ at risk in a linear-quadratic BED model.

The marker 50 is positioned at a location on the 2D graph 42 of FIG. 2 defined by a current total dose $D_{curr}=45$ Gy (i.e. X=45 Gy) and a current total squared dose $SD_{curr}=405$ Gy$^2$, corresponding to $N_{curr}=5$ fractions with fractional doses $d_t=9$ Gy. The user can readily explore other possible fractionation/total dose combinations merely by moving the marker 50 to other locations, e.g. using a mouse pointer 51 controlled by the mouse 19 or, in the case of a touchscreen, touching the location on the display 16 where the user wishes to position the marker. Upon detection of user selection of a new location ($X_{new}$, $Y_{new}$) on the 2D graph 42 made via a user input component comprising a pointing device (e.g. mouse 19), a new value for the current total dose $D_{curr}$ and the current total squared dose $SD_{curr}$ are computed from $X_{new}$ and $Y_{new}$ using the equality of X and Y with the total dose D and the total squared dose SD respectively (or, more generally, using proportionality of X and Y with D and SD respectively, since the X-Y plane could have various scalings to account for chosen dose units or so forth). The new value for the current number of fractions $N_{curr}$ and the current fractional doses $d_{t,curr}$ are computed from the new values of the current total dose $D_{curr}$ and current total squared dose $SD_{curr}$.

In a variant embodiment, the 2D graph 42 can display two markers 50 (second marker not shown in FIGS. 1 and 2), one corresponding to the current fractionation scheme defined by ($X_{curr}$, $Y_{curr}$), and one corresponding to a user selected new location ($X_{new}$, $Y_{new}$). This second marker can show additional information on the selected new fractionation scheme, such as the corresponding fraction number $N_{new}$ and fractional dose values $d_t$, as well as comparative advantages versus disadvantages of the new fractionation scheme with respect to the current fractionation scheme. Such information may include additional BED to the tumor, BED sparing of OARs, BED equivalent additional physical dose to the tumor if it was given in the current fractionation scheme, BED equivalent physical dose sparing of OARs if it was given in the current fractionation scheme, etc.

In a variant embodiment, the 2D graph 42 has a discretization grid comprising the set of parabolic curves defined by the set of integers in the inclusive range [$N_{min}$, $N_{max}$] assuming uniform fractionation, i.e. equal fractional dose values, and the user selection of a new location ($X_{new}$, $Y_{new}$) is locked to the nearest parabola representing the nearest integer N. Other guidance can be provided, such as not accepting a new location ($X_{new}$, $Y_{new}$) that is outside of the feasible range bounded by $N_{min}$ and $N_{max}$.

Additionally or alternatively, a further graphical guide that can be shown to display on the 2D graph 42 a parabolic curve defined by a target fraction number $N_{target}$ (where $N_{min} \leq N_{target} \leq N_{max}$). Such a parabola can show the clinician the range of values attainable for the target fraction $N_{target}$ assuming uniform fractional doses.

In some embodiments, the fractional optimization tool 40 is used to actually set the fractionation and the total dose. In these embodiments, the user indicates via the at least one user input component that the current total dose $D_{curr}$ and current total squared dose $SD_{curr}$, as well as the implicitly defined current number of fractions $N_{curr}$ and current fractional doses $d_{t,curr}$ are final. Alternatively, the fractional optimization tool 40 may be used as an exploration tool to explore the space of feasible fractionation/total dose settings, with the final values being manually chosen by the user (e.g. typed into a radiation therapy physician's order).

Figure 3:
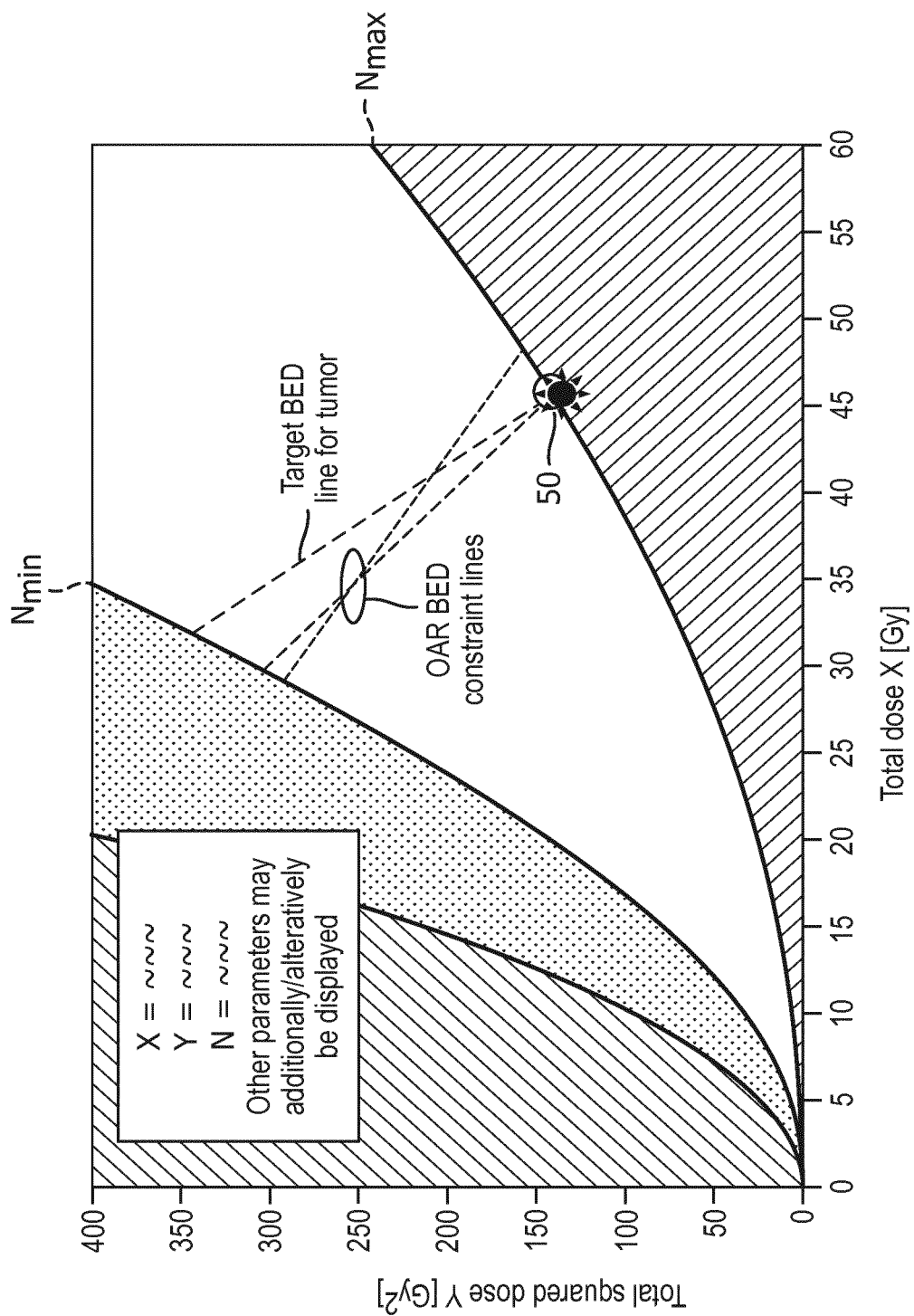
Figure 4:
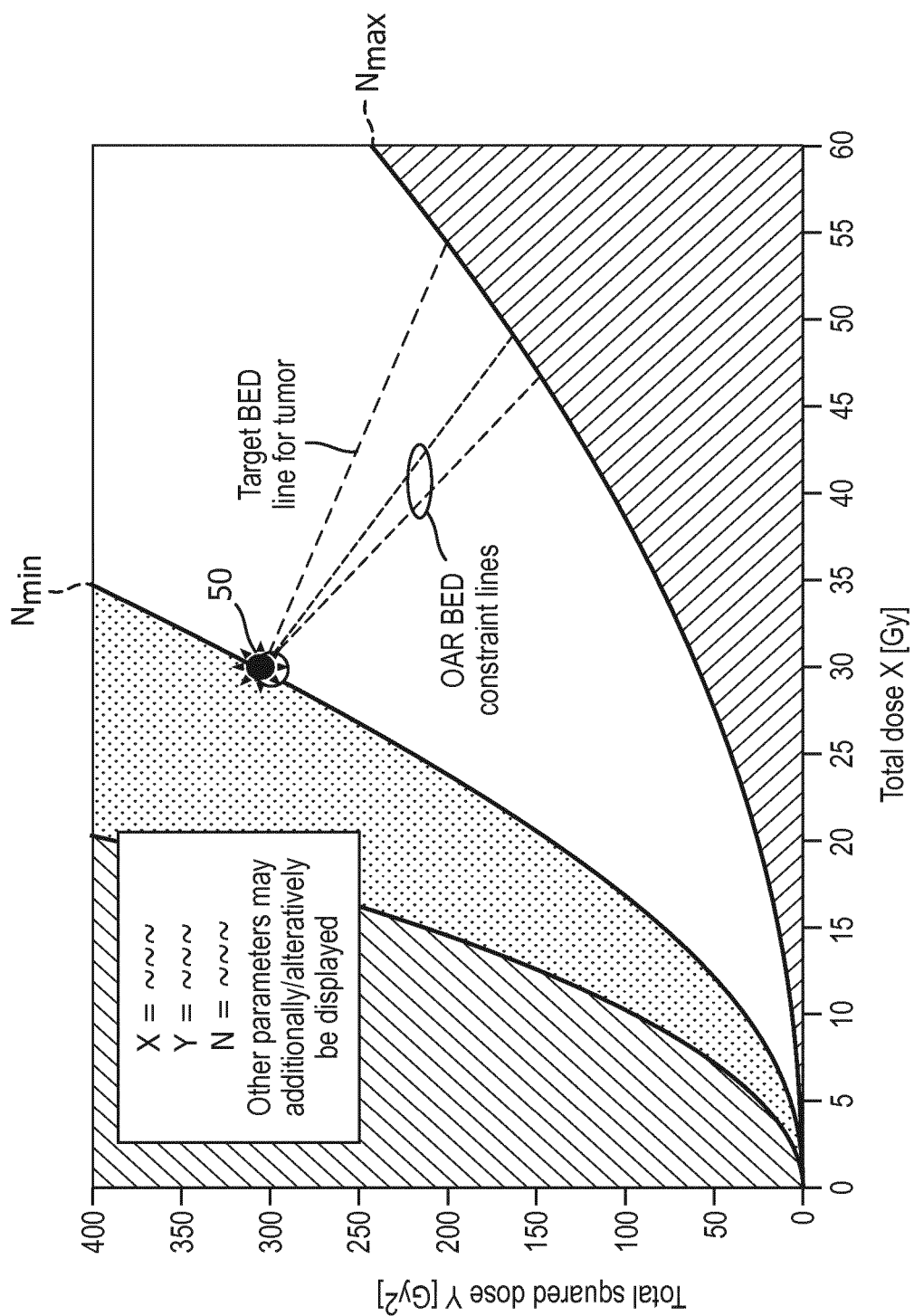
Figure 5:
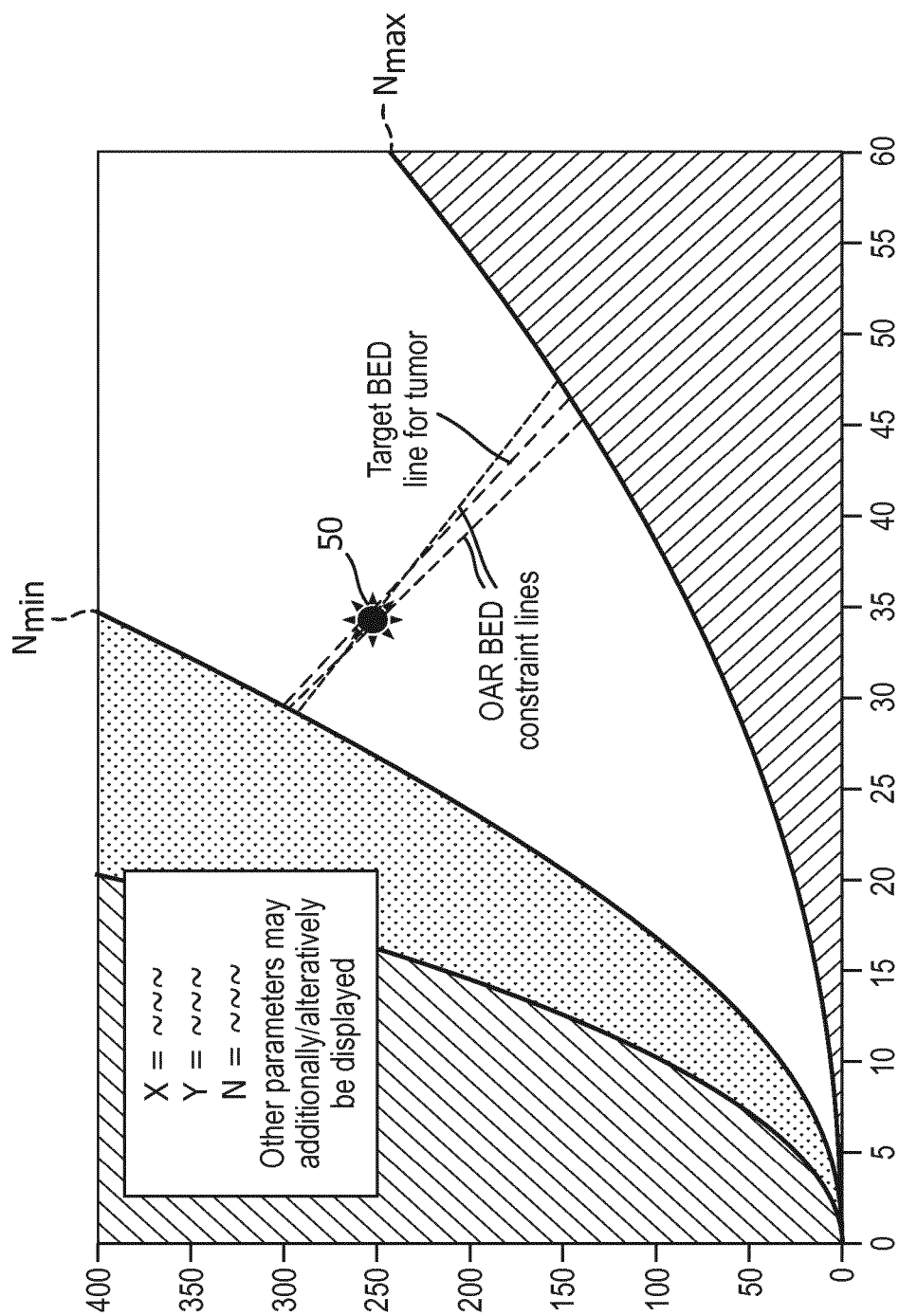

With reference now to FIGS. 3-5, some illustrative examples are shown. In FIG. 3 a case is displayed where hyperfractionation is optimal. As can be seen the constraint lines are all less steep than the tumor BED line, i.e. where:

$$\max_{m \in M} \frac{1}{\rho^m \sigma^m} < \frac{1}{\rho^T \sigma^T}$$

holds. Hence to maximize the tumor BED the corresponding "Tumor" line in FIG. 3 is moved as much to the right as possible, which corresponds to giving as many equal dosage fractions as possible (in this case equality occurs in the lower constraint in Equation (33).

In FIG. 4 a case is displayed where hypofractionation is optimal. This corresponds to the situation where all constraint lines are steeper than the tumor BED line, i.e. where:

$$\min_{m \in M} \frac{1}{\rho^m \sigma^m} > \frac{1}{\rho^T \sigma^T}$$

To maximize the tumor BED its line in FIG. 4 is moved as much to the top as possible, which corresponds to hypofractionation. The optimum is reached at the minimum number of fractions $N_{min}$.

FIG. 5 displays a case where neither hyper- nor hypo fractionation is optimal. This corresponds to the situation where:

$$\min_{m \in M} \frac{1}{\rho^m \sigma^m} < \frac{1}{\rho^T \sigma^T} < \max_{m \in M} \frac{1}{\rho^m \sigma^m}$$

The OAR constraints that form the boundary are all represented by straight lines having an increasing steepness (i.e. if we go through them according to their abscissas, a constraint with a higher abscissa value also has a higher steepness). Since the tumor BED is again increased as we move its line to right and up in FIG. 3, the optimum is at the intersection of the two constraints for which:

$$\frac{1}{\rho^p \sigma^p} \leq \frac{1}{\rho^T \sigma^T} \wedge \forall m \in M: \frac{1}{\rho^p \sigma^p} < \frac{1}{\rho^m \sigma^m} \leq \frac{1}{\rho^T \sigma^T} \quad (34)$$

$$\frac{1}{\rho^T \sigma^T} \leq \frac{1}{\rho^q \sigma^q} \wedge \forall m \in M: \frac{1}{\rho^T \sigma^T} \leq \frac{1}{\rho^m \sigma^m} < \frac{1}{\rho^q \sigma^q} \quad (35)$$

As discussed previously, any (X, Y) pair in the feasible region between $N_{min}$ and $N_{max}$ can be achieved by having only two distinct dose per fraction values. An easy choice is to allow only $N_{low}=1$ low dose fractions and try to approximate a uniform fractionation scheme. Supposing that the (X, Y) intersection point is located between the N and N+1 fraction uniform schemes, the appropriate dose values are:

$$d_{high} = \frac{X + \sqrt{1/(N-1)(NY - X^2)}}{N} \quad (36)$$

$$d_{low} = \frac{X - \sqrt{(N-1)(NY - X^2)}}{N}. \quad (37)$$

To use the developed fractionation optimization tool the following information serves as input. The dose distribution for the treatment is one input. Since only the temporal aspect of the treatment is optimized, the dose sparing factors in the voxels is sufficient, which can be obtained from scaling the dose distribution to some reference value. A convenient choice is to use the mean dose in the target region (identified as all regions belonging to the GTVs in the current implementation), but one could use an entered prescription dose as well.

A further input is the dose constraints for the different organs. The optimal fractionation scheme depends on what OAR constraints are considered acceptable by the physician. In the illustrative examples a fixed set of constraints were used, focusing on liver cases, however an option can be provided to allow a user to interactively enter a chosen set of constraints for a choice of OARs (with the limitation that for the same constraint at most two dose values can be given for two distinctive fraction numbers, as discussed previously).

A further input is the OAR structures and their corresponding index map (e.g. the set of voxels belonging to the structures) in order to associate the different parts of the patient anatomy with the appropriate OARs to obtain the generalized dose sparing factors and BED tolerances. A further input is the minimum and maximum number of fractions, as well as optionally the number of low dose fractions a physician would consider (otherwise it is simply set to 1).

The 2D graph 42 is preferably implemented as an interactive, "clickable" GUI, in which the user selects a new location and the dose and fractionation is computed. This allows physicians to choose a permissible point on the map, for which all relevant dose constraint values could be calculated on-the-fly and displayed (e.g. as an equivalent dose difference from the nominal scenario, as explained previously).

In the illustrative examples, the OAR constraints are treated as "objectives", in the sense that they do not necessarily have to be satisfied (e.g., in FIG. 2 the selected location of the marker 50 is above the strictest T1 liver constraint line, meaning that the T1 constraint is not satisfied although alternative looser constraints T2-T5 are satisfied. This generally conforms to clinical practice, where certain OAR constraints may considered "hard", i.e. that they always have to be fulfilled, while others are "soft", which a treatment plan only aims to achieve.

In general, the one or more computers 14, 28 are operatively connected with at least one non-transitory storage medium that stores instructions readable and executable by the computer(s) to perform the disclosed fractionated radiation therapy planning operations. The at least one non-transitory storage medium may, for example, include a hard disk or other magnetic storage medium, an optical disk or other optical storage medium, a solid state drive, flash memory, or other electronic storage medium, various combinations thereof, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A fractionated radiation therapy planning device comprising:
  a computer including a display component and at least one user input component; and
  at least one non-transitory storage medium storing instructions readable and executable by the computer to perform fractionated radiation therapy planning operations including:
    generating or receiving fractionation selection inputs including at least a radiation dose distribution to be delivered by the fractionated radiation therapy and organ-at-risk (OAR) Biologically Effective Dose (BED) constraints for one or more organs-at-risk, each OAR BED constraint representing a maximum BED that can be delivered by the fractionated radiation therapy to the corresponding OAR;
    displaying a two-dimensional (2D) graph of a parameter X equal to or proportional to $D = \sum_{t=1}^{N} d_t$ versus a parameter Y equal to or proportional to $SD = \sum_{t=1}^{N} d_t^2$ where N is a number of fractions for delivering the dose distribution, total dose D is a total radiation dose to be delivered by the fractionated radiation therapy, and $d_t$ is the fractional dose of the total radiation dose D to be delivered in the fraction t;
    displaying on the 2D graph OAR BED lines depicting each OAR BED constraint;
    displaying on the 2D graph a marker at a location on the 2D graph defined by a current total dose $D_{curr}$ and a current total squared dose $SD_{curr}$; and
    receiving via the at least one user input component a new value for at least one of the current total dose $D_{curr}$ and the current total squared dose $SD_{curr}$ and updating the displaying of the marker in accord with the updated values of the current total dose $D_{curr}$ and the current total squared dose $SD_{curr}$.

2. The fractionated radiation therapy planning device of claim 1 wherein the fractionation selection inputs further include a target BED for a tumor which is a target BED to be delivered by the fractionated radiation therapy to the tumor, and the fractionated radiation therapy planning operations further include:
  displaying on the 2D graph a target BED line depicting the target BED for the tumor.

3. The fractionated radiation therapy planning device of claim 2 wherein the target BED line depicting the target BED for the tumor is given by:

$$\sigma^T X + \rho^T (\sigma^T)^2 Y = B^T$$

where $B^T$ is the target BED to be delivered by the fractionated radiation therapy to the tumor, $\sigma^T$ is a constant, and $\rho^T$ is the inverse of the α/β ratio of the tumor in a linear-quadratic BED model.

4. The fractionated radiation therapy planning device of claim 1 wherein the OAR BED line depicting OAR BED constraint m is given by:

$$\sigma^m X + \rho^m (\sigma^m)^2 Y = B^m$$

where $B^m$ is the OAR BED constraint, $\sigma^m$ is a constant, and $\rho^m$ is the inverse of the α/β ratio of the corresponding organ-at-risk in a linear-quadratic BED model.

5. The fractionated radiation therapy planning device of claim 1 wherein the fractionated radiation therapy planning operations further include:
  computing a current number of fractions $N_{curr}$ for a fractionation scheme from the current total dose $D_{curr}$ and the current total squared dose $Y_{curr}$; and
  updating the current number of fractions $N_{curr}$ for the fractionation scheme from the updated values of the current total dose $D_{curr}$ and the current total squared dose $SD_{curr}$.

6. The fractionated radiation therapy planning device of claim 5 wherein the fractionation scheme employs uniform fractional doses.

7. The fractionated radiation therapy planning device of claim 1 wherein the generated or received fractionation selection inputs further include a maximum number of fractions $N_{max}$ and a minimum number of fractions $N_{min}$, and the fractionated radiation therapy planning operations further include:
  displaying on the 2D graph parabolic boundary curves indicating the maximum number of fractions $N_{max}$ and the minimum number of fractions $N_{min}$;
  wherein the BED lines are displayed only in an operational region bounded by the parabolic boundary curves indicating the maximum number of fractions $N_{max}$ and the minimum number of fractions $N_{min}$ assuming uniform fractional doses.

8. The fractionated radiation therapy planning device of claim 7 wherein the 2D graph has a discretization grid comprising the set of parabolic curves defined by the set of integers in the inclusive range [$N_{min}$, $N_{max}$] assuming uniform fractional doses.

9. The fractionated radiation therapy planning device of claim 1 wherein the generated or received fractionation selection inputs further include a maximum number of fractions $N_{max}$ and a minimum number of fractions $N_{min}$, and the fractionated radiation therapy planning operations further include:
   displaying on the 2D graph a parabolic curve defined by a target fraction number $N_{target}$ where $N_{min} \leq N_{target} \leq N_{max}$, assuming uniform fractional doses.

10. The fractionated radiation therapy planning device of claim 1 wherein the fractional dose $d_t$ of the total radiation dose D to be delivered in each fraction t, other than any low dose fraction, are the same.

11. The fractionated radiation therapy planning device of claim 10 wherein the generated or received fractionation selection inputs further include a maximum number of fractions $N_{max}$ and a minimum number of fractions $N_{min}$, and the receiving via the at least one user input component of a new value for at least one of the current total dose $D_{curr}$ and the current total squared dose $Y_{curr}$ includes:
   detecting user selection of a location ($X_{new}$, $Y_{new}$) on the 2D graph made via a user input component comprising a pointing device;
   computing the new value for the current total dose $D_{curr}$ and the current total squared dose $SD_{curr}$ from $X_{new}$ and $Y_{new}$ respectively using their equality or proportionality; and
   computing the new value for a current number of fractions $N_{curr}$ and current fractional dose values $d_{t,curr}$ from the new values of the current total dose $D_{curr}$ and the current total squared dose $SD = \sum_{t=1}^{N} d_t^2$ under the constraint that $N_{curr}$ is an integer in the inclusive range [$N_{min}$, $N_{max}$] and assuming a single low dose fraction $N_{low} = 1$.

12. The fractionated radiation therapy planning device of claim 10 wherein the fractionated radiation therapy planning operations further include:
   receiving via the at least one user input component an indication that the current total dose $D_{curr}$ and the current total squared dose $SD_{curr}$ are final;
   setting the final fractionation to the current fractionation $N_{curr}$; and
   setting the final fractional doses $d_t$ to $d_{high}$ for $N_{curr} - 1$ number of fractions and to $d_{low}$ for the single low dose fraction.

13. A non-transitory storage medium storing instructions readable and executable by a computer including a display component and at least one user input component to perform fractionated radiation therapy planning operations including:
   generating or receiving fractionation selection inputs including at least a radiation dose distribution to be delivered by the fractionated radiation therapy, biologically effective dose (BED) constraints for one or more organs-at-risk wherein each BED constraint is a constraint on the BED that can be delivered by the fractionated radiation therapy to the corresponding organ at risk, and a target BED for a tumor which is a target BED to be delivered by the fractionated radiation therapy to the tumor;
   displaying a two-dimensional (2D) graph of a parameter X equal to or proportional to a total radiation dose D to be delivered by the fractionated radiation therapy versus a parameter Y equal to or proportional to a total squared dose SD;
   displaying on the 2D graph BED lines depicting each BED constraint and the target BED; and
   displaying on the 2D graph a marker at a location on the 2D graph defined by a current total dose $D_{curr}$ and a current total squared dose $SD_{curr}$;
   determining a current number of fractions $N_{curr}$ for a fractionation scheme from the current total dose $D_{curr}$ and the current total squared dose $SD_{curr}$; and
   providing for moving the marker in response to user inputs via the at least one user input component whereby the current total dose $D_{curr}$, the current total squared dose $SD_{curr}$, and the current number of fractions $N_{curr}$ are adjustable by the user.

14. The non-transitory storage medium of claim 13 wherein the fractionation scheme employs uniform fractional doses.

15. The non-transitory storage medium of claim 13 wherein the fractionated radiation therapy planning operations further include:
   displaying on the 2D graph a second marker at a user selected location defined by a new total dose $D_{new}$ and a new total squared dose $SD_{new}$; and
   determining a new number of fractions $N_{new}$ for the fractionation scheme or for a new fractionation scheme from the new total dose $D_{new}$ and the new total squared dose $SD_{new}$.

16. The non-transitory storage medium of claim 13 wherein:
   the target BED line depicting the target BED for the tumor is given by $\sigma^T X + \rho^T (\sigma^T)^2 Y = B^T$ where $B^T$ is the target BED to be delivered by the fractionated radiation therapy to the tumor, $\sigma^T$ is a constant, and $\rho^T$ is the inverse of the $\alpha/\beta$ ratio of the tumor in a linear-quadratic BED model; and
   the constraint BED line depicting BED constraint m is given by $\sigma^m X + \rho^m (\sigma^m)^2 Y = B^m$ where $B^m$ is the constraint on the BED to be delivered by the fractionated radiation therapy to the corresponding organ at risk, $\sigma^m$ is a constant, and $\rho^m$ is the inverse of the $\alpha/\beta$ ratio of the corresponding organ at risk in a linear-quadratic BED model.

17. The non-transitory storage medium of claim 13 wherein the generated or received fractionation selection inputs further include a maximum number of fractions $N_{max}$ and a minimum number of fractions $N_{min}$, and the fractionated radiation therapy planning operations further include:
   displaying on the 2D graph parabolic boundary curves indicating the maximum number of fractions $N_{max}$ and the minimum number of fractions $N_{min}$ assuming uniform fractional doses;
   wherein the BED lines are displayed only in an operational region bounded by the parabolic boundary curves indicating the maximum number of fractions $N_{max}$ and the minimum number of fractions $N_{min}$.

18. The non-transitory storage medium of claim 13 wherein the fractionated radiation therapy planning operations further include:
   displaying on the 2D graph a parabolic curve defined by the current fractionation $N_{curr}$ assuming uniform fractional doses.

19. A fractionated radiation therapy planning method comprising:
   generating or receiving fractionation selection inputs including at least a radiation dose distribution to be delivered by the fractionated radiation therapy and a plurality of Biologically Effective Dose (BED) targets and/or constraints;

displaying, on a display component, a two-dimensional (2D) graph of a parameter X equal to or proportional to $D=\Sigma_{t=1}^{N}d_{t}$ versus a parameter Y equal to or proportional to $SD=\Sigma_{t=1}^{N}d_{t}^{2}$ where N is a number of fractions for delivering the dose distribution, total dose D is a total radiation dose to be delivered by the fractionated radiation therapy, and $d_t$ is the fractional dose of the total radiation dose D to be delivered in fraction t;

displaying on the 2D graph BED lines depicting each BED target or constraint;

displaying on the 2D graph a marker at a location on the 2D graph; and providing for adjustment, using at least one user input component, of the location of the marker to optimize the total dose D, the number of fractions N, and the fractional doses $d_t$, including providing a processor programmed to generate new values for the number of fractions N, total dose D, and the fractional doses $d_t$ in response to selection of a new location for the marker on the 2D graph;

wherein the number of fractions N is computed for a fractionation scheme from the total dose D and the total squared dose SD indicated by the location of the marker.

20. The fractionated radiation therapy planning method of claim 19 wherein the generated or received fractionation selection inputs further include a maximum number of fractions $N_{max}$ and a minimum number of fractions $N_{min}$, and the method further comprises:

displaying on the 2D graph parabolic boundary curves indicating the maximum number of fractions $N_{max}$ and the minimum number of fractions $N_{min}$, assuming uniform fractional doses;

wherein the BED lines are displayed only in an operational region bounded by the parabolic boundary curves indicating the maximum number of fractions $N_{max}$ and the minimum number of fractions $N_{min}$.

* * * * *